United States Patent
Ng et al.

(10) Patent No.: US 10,070,049 B2
(45) Date of Patent: Sep. 4, 2018

(54) METHOD AND SYSTEM FOR CAPTURING AN IMAGE FOR WOUND ASSESSMENT

(71) Applicant: Konica Minolta Laboratory U.S.A., Inc., San Mateo, CA (US)

(72) Inventors: Kim Chai Ng, San Mateo, CA (US); Xiaonong Zhan, San Mateo, CA (US); Wei Ming, San Mateo, CA (US)

(73) Assignee: KONICA MINOLTA LABORATORY U.S.A., INC, San Mateo, CA (US)

( * ) Notice: Subject to any disclaimer, the term of this patent is extended or adjusted under 35 U.S.C. 154(b) by 443 days.

(21) Appl. No.: 14/877,352

(22) Filed: Oct. 7, 2015

(65) Prior Publication Data
US 2017/0104925 A1   Apr. 13, 2017

(51) Int. Cl.
*A61B 5/00* (2006.01)
*H04N 5/232* (2006.01)
*H04N 5/247* (2006.01)
*G06F 3/0482* (2013.01)

(52) U.S. Cl.
CPC ....... *H04N 5/23222* (2013.01); *A61B 5/0077* (2013.01); *A61B 5/445* (2013.01); *A61B 5/743* (2013.01); *A61B 5/7435* (2013.01); *G06F 3/0482* (2013.01); *H04N 5/23216* (2013.01); *H04N 5/23293* (2013.01); *H04N 5/247* (2013.01); *A61B 2560/0475* (2013.01)

(58) Field of Classification Search
CPC .......... A61B 5/00; A61N 5/06; A61N 5/0613; G02B 21/365; G01B 11/00
See application file for complete search history.

(56) References Cited

U.S. PATENT DOCUMENTS

| | | | |
|---|---|---|---|
| 2006/0111761 A1* | 5/2006 | Butler | A61N 5/0613 607/88 |
| 2010/0041998 A1 | 2/2010 | Postel | |
| 2012/0033867 A1 | 2/2012 | Christiansen, II et al. | |
| 2014/0085453 A1* | 3/2014 | Yamane | G02B 21/365 348/79 |
| 2014/0088402 A1 | 3/2014 | Xu | |
| 2014/0243619 A1 | 8/2014 | Fright et al. | |

FOREIGN PATENT DOCUMENTS

WO     2012/083349 A1     6/2012

OTHER PUBLICATIONS

International Search Report and Written Opinion dated Jan. 26, 2017 by the International Searching Authority (9 pages).

\* cited by examiner

*Primary Examiner* — Sathyanaraya V Perungavoor
*Assistant Examiner* — Patricia I Young
(74) *Attorney, Agent, or Firm* — Buchanan Ingersoll & Rooney PC

(57) ABSTRACT

A method is disclosed of capturing an image of a wound on a subject for wound assessment. The method includes obtaining an image of a portion of the subject with one or more cameras; displaying the image on a display panel on an imaging device; obtaining a stored condition from a memory; obtaining a present condition; comparing the stored condition and the present condition; displaying a crosshair over the image on the display panel when it is decided that the present condition corresponds to the stored condition on the basis of the comparison; receiving an instruction for capturing; and capturing an image of the wound in response to the received instruction.

18 Claims, 18 Drawing Sheets

Condition select menu

| | |
|---|---|
| Record | Thomas : right foot |
| patient | Thomas |
| Wound location | right foot |
| Distance | xxxx |
| Angle | yyyy |
| Lightness | zzzz |

| | |
|---|---|
| Record | Thomas : back |
| patient | Thomas |
| Wound location | back |
| Distance | aaaa |
| Angle | bbbb |
| Lightness | cccc |

Stored condition data

| | | | |
|---|---|---|---|
| Record | Thomas : right foot1 | Record | Thomas : back1 |
| Capture date | 2015.m1.d1 | Capture date | 2015.m4.d4 |
| Patient | Thomas | Patient | Thomas |
| Wound location | right foot | Wound location | back |
| Wound width | xxxx1 | Wound width | aaaa4 |
| Wound height | yyyy1 | Wound height | bbbb4 |
| Wound depth | zzzz1 | Wound depth | cccc4 |
| Wound shape | vvvvv1.bmp | Wound shape | dddd4.bmp |

| | | | |
|---|---|---|---|
| Record | Thomas : right foot2 | Record | Thomas : back2 |
| Capture date | 2015.m2.d2 | Capture date | 2015.m5.d5 |
| Patient | Thomas | Patient | Thomas |
| Wound location | right foot | Wound location | back |
| Wound width | xxxx2 | Wound width | aaaa5 |
| Wound height | yyyy2 | Wound height | bbbb5 |
| Wound depth | zzzz2 | Wound depth | cccc5 |
| Wound shape | vvvvv2.bmp | Wound shape | dddd5.bmp |

．  ．
．  ．
．  ．

Wound detection history data

Fig. 7

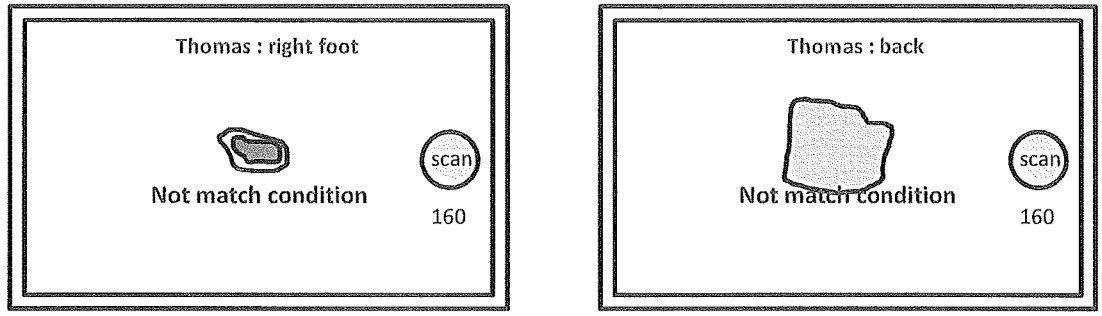

The crosshair is not displayed if the present capturing environment does not correspond to the stored condition.

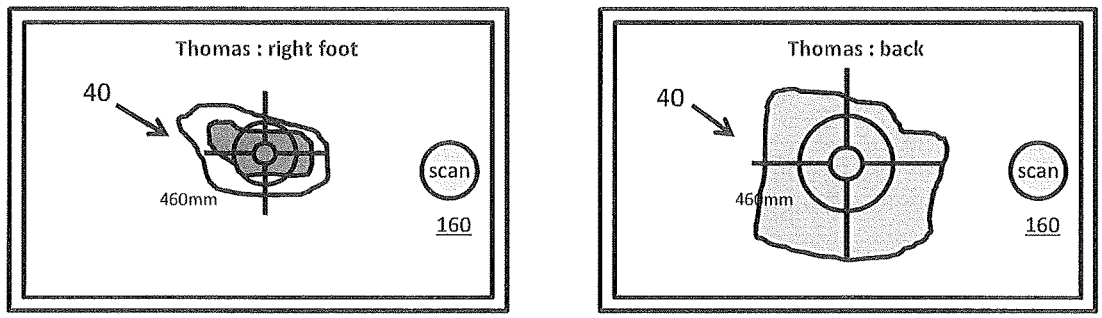

The crosshair is displayed if the present capturing environment corresponds to the stored condition.
In addition, the distance between the 3D camera and the wound is displayed.

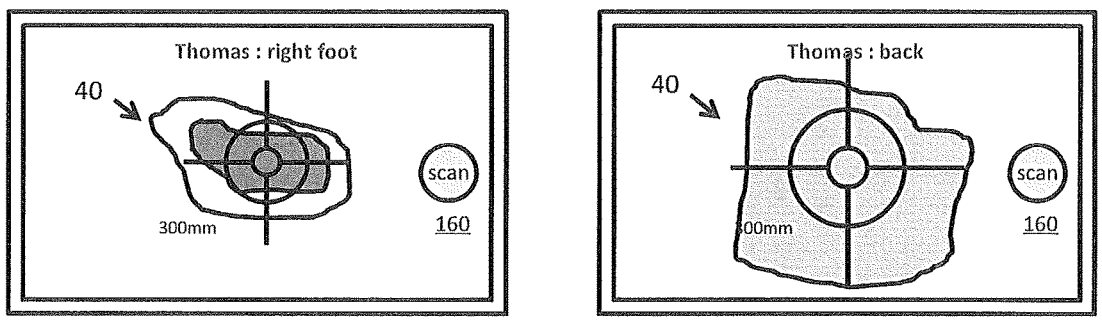

In response to moving the device close to the wound, the wound image is magnified.
The size of the crosshair is also magnified so that the size consists with a predetermined actual length.

Fig. 8

Variation of shape of bounding volume

METHOD AND SYSTEM FOR CAPTURING AN IMAGE FOR WOUND ASSESSMENT

FIELD OF THE INVENTION

The present invention relates to a device and method for wound assessment, and more particularly, to a method and system for capturing visible injuries or wounds, and which allows both clinicians and patients to capture wounds relatively easily and consistently at different times and/or locations for wound assessment.

BACKGROUND OF THE INVENTION

For many wound types, like pressure ulcers, the recovery time can be very long. To track the wound progress and get proper treatment, the first step is to capture the wound properly. Considering many actual issues, like wound location (for example, back, head), position (for example, lying down, sitting), environment (for example, lighting, supporting device), and experience of using electronic devices (for example, angle, focus) can greatly affect capturing results. It is also common to ask the user or operator to capture an image in certain conditions, like perpendicular to a wound within certain range. However, this can be difficult for an inexperience user, especially if a patient has to capture a wound by him or herself.

SUMMARY OF THE INVENTION

In view of the above, it would be desirable to have a device and method, which provides relatively clear and dynamic indications to a user by displaying instructions on the device to help guide the user for capturing images of the visible injury or wound.

A method is disclosed of capturing an image of a wound on a subject for wound assessment, the method comprising: obtaining an image of a portion of the subject with one or more cameras; displaying the image on a display panel on an imaging device; obtaining a stored condition from a memory; obtaining a present condition; comparing the stored condition and the present condition; displaying a crosshair over the image on the display panel when it is decided that the present condition corresponds to the stored condition on the basis of the comparison; receiving an instruction for capturing; and capturing an image of the wound in response to the received instruction.

A computer program product comprising a non-transitory computer usable medium having a computer readable code embodied therein is disclosed for capturing an image of a wound on a subject for wound assessment, the process comprising: obtaining an image of a portion of the subject with one or more cameras; displaying the image on a display panel on an imaging device; obtaining a stored condition from a memory, the stored condition including at least one of distance data, angle data, and lightness data; obtaining a present condition; comparing the stored condition and the present condition; displaying a crosshair over the image on the display panel when it is decided that the present condition corresponds to the stored condition on the basis of the comparison; receiving an instruction for capturing; and capturing an image of the wound in response to the received instruction.

An imaging device is disclosed, the imaging device comprising: one or more cameras configured to obtain an image of a portion of the subject with one or more cameras; displaying the image on a display panel on the imaging device; and a processor configured to: obtain a stored condition from a memory; obtain a present condition; compare the stored condition and the present condition; display a crosshair over the image on the display panel when it is decided that the present condition corresponds to the stored condition on the basis of the comparison; receive an instruction for capturing; and capture an image of the wound in response to the received instruction.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

FIG. 7 is an illustration showing wound detection history in accordance with an exemplary embodiment.

FIG. 8 is an illustration of a series of images depicted on the user interface in accordance with an exemplary embodiment.

DESCRIPTION OF THE PREFERRED EMBODIMENTS

Figure 1:
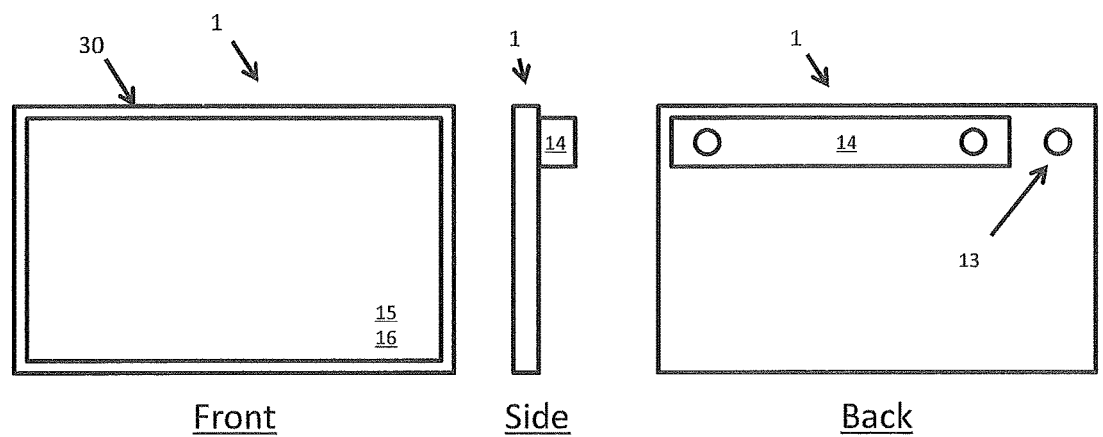
FIG. 1 is an illustration of an imaging device for wound assessment with a graphical user interface in accordance with an exemplary embodiment.

Reference will now be made in detail to the present preferred embodiments of the invention, examples of which are illustrated in the accompanying drawings. Wherever possible, the same reference numbers are used in the drawings and the description to refer to the same or like parts.

In accordance with an exemplary embodiment, a device and method are disclosed, which can automatically or semi-automatically detect wounds and/or visible injuries, can track wounds and display the distance to the wound, can include a capture range and shape to help ensure relatively high quality and low computation cost, and highlights the wound, if captured.

In accordance with an exemplary embodiment, the capturing process can include, for example, detecting a wound or visible injury, tracking the wound or visible injury, providing a capture range and shape; and highlighting the wound or visible injury.

Wound Detection:

A wound can be detected by a number of features, which can include:

Color: Wounds are typically red/pink/yellow/black in color depending on the stages of the wound deteriorating or healing progress. The wound color is different from a patient's skin tone.

Contrast: Since the wound color differs from the normal skin tone, this contrast yields edge contours. A closed contour can be detected and analyzed to find the wound's boundary.

Texture: Wound may have more roughness than a smooth skin.

Surface normal: Wound's surface often sits lower or higher than the surrounding normal skin. The surface normal thus can be used to detect, for example, a recess or a sudden change in the surface normal at the recessed wound boundary.

3D depth: Since the wound often sits lower or higher than the surround normal skin, the depth information can be used to find an area that is lower than the skin surface.

In accordance with an exemplary embodiment, when a wound is detected, a bounding volume, in the shape of cuboid, sphere, or ellipsoid, representing the capturing range for which a 3D image is constructed can be displayed and a crosshair 40 (FIG. 8) can point to the center of the wound. For example, the crosshair can be represented as intersecting lines in the shape of a cross, "+", and/or variations, which can include dots, posts, circles, scales, chevrons, or a combination of these.

In accordance with an exemplary embodiment, for example, if there are multiple wounds, or the device fails to detect the wound, the user or operator can manually move the crosshair.

Wound Tracking:

In accordance with an exemplary embodiment, the wound can be tracked by detecting the above-mentioned features. Other scale-invariant features such as SIFT, SURF, or BRISK can also be used to provide stable tracking points. In addition to the feature-based techniques, area-based method such as cross-correlation can be used to locate the wound in the consecutive frames. For example, Kalman filtering, which incorporates prior information about the scene or object, can also be used to overcome the case of partial wound occlusion.

In accordance with an exemplary embodiment, the crosshair can or always point to the center of the wound, and the distance from the center of the wound to the camera can be displayed. In addition, a two-dimensional (2D) display size of the crosshair can be expanded or contracted with respect to a depth (or Z distance), wherein X, Y coordinates are displayed. For example, in accordance with an exemplary embodiment, the X, Y, and Z values can be derived from the mapping of camera matrix, model matrix, and view matrix.

Capture Range and Shape:

In accordance with an exemplary embodiment, when a visible wound is detected, the size and shape of wound range can be roughly estimated based on contour found using the features described above in connection with the wound detection. The initial cube for capturing range for which a 3D image is constructed will be adaptively modified to a larger or smaller cube, or to a cuboid, sphere, or ellipsoid with the suitable size (length, width, height) to match the wound shape, and help reduce the data associated with the detection and reduce unnecessary data in connection with the wound as detected.

Highlight Wound:

In accordance with an exemplary embodiment, a wound may be large and it may not be flat throughout and with the possibility of occluded views, and as such, one capturing frame may not be sufficient to scan and/or see the entirety of the wound. For example, in accordance with an exemplary embodiment, the user and/or operator can move (shift, tilt, or/and rotate) the camera to help ensure that the entirety of the wound can be fully captured. In this capturing process, when a part of wound has been scanned and the data has been successfully acquired, that part of wound will be highlighted with a chosen color, which is obviously different from the to-be scanned regions, to give the user a visual feedback. For example, in accordance with an exemplary embodiment, the highlight can help enable the user to know where next the camera should be moved to for a full wound capture.

FIG. 1 is an illustration of an imaging device 1 for wound assessment with a graphical user interface in accordance with an exemplary embodiment. As shown in FIG. 1, the device 1 can include a graphical user interface or screen 15, which preferably defines a touch screen or panel 16 on a front side. The device 1 can also include one or more cameras 13, 14, preferably in the form of a two-dimensional (2D camera) 13 and a three-dimensional (3D) camera 14 on a back side. For example, the imaging device 1 can be a tablet computer, for example, an iPhone®, an iPad®, Android enabled devices and/or other various handheld mobile devise as described herein, which includes one or more cameras having the ability to capture and generate 3D images.

As shown in FIG. 1, the device 1 can be a tablet or tablet-like device having the user interface or display 15 and an outer housing 30. Electrical components as disclosed herein may be positioned between the user interface or display 15 and the housing. The electronic components may vary depending on the particular functionality of the device 1. However, by way of example, the electronic components may include, for example, a battery, a communication interface, an antenna, a processor, and/or a memory.

Figure 2A:
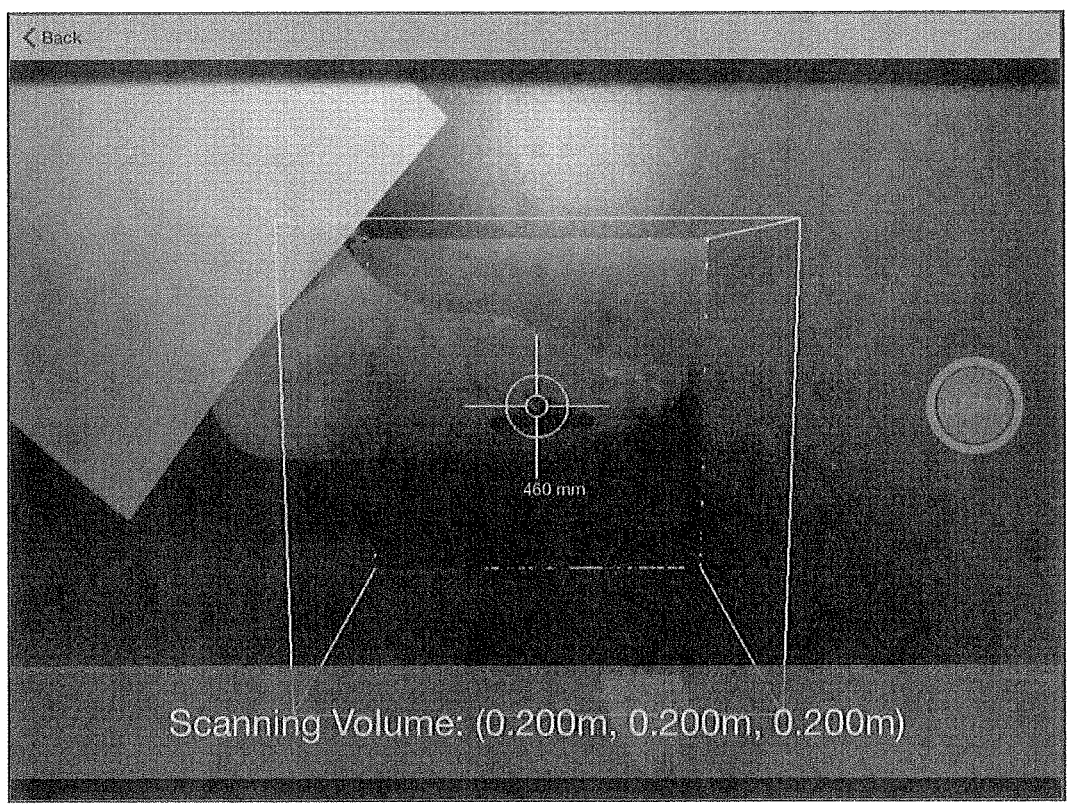
FIGS. 2A and 2B are illustrations of an image on the graphical user interface or display screen in accordance with an exemplary embodiment.
Figure 2B:
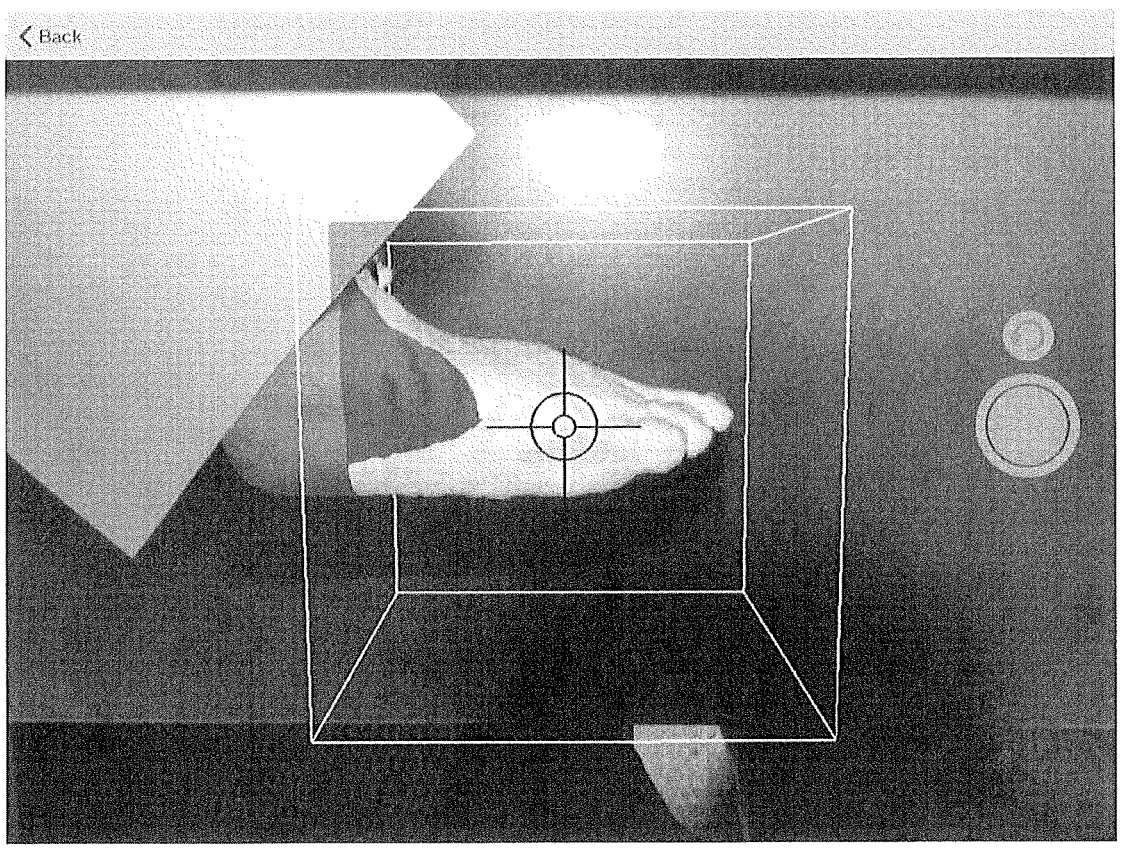

FIGS. 2A and 2B are illustrations of an image on the graphical user interface or display screen in accordance with an exemplary embodiment. As shown in FIGS. 2A and 2B, the user places a portion or part of his or her body with the wound or injury in front of the cameras 13, 14 and an image is displayed on the user interface or screen 15, which includes a crosshair, which points to the center of the wound, a distance from the wound center to the cameras 13, 14 and a border of the capturing range for which a 3D image is constructed.

Figure 3:
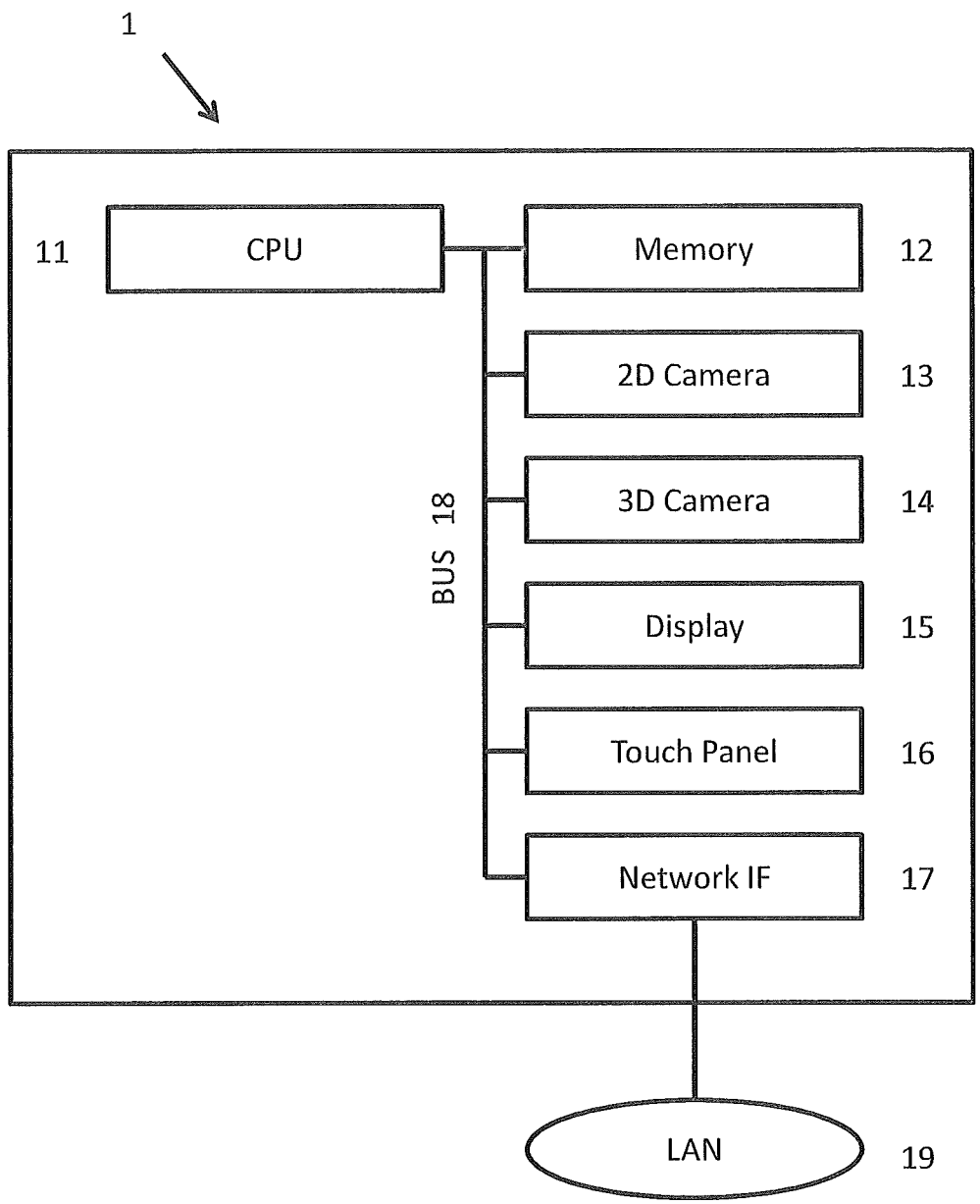
FIG. 3 is an illustration of a block diagram of a device for wound assessment in accordance with an exemplary embodiment.

FIG. 3 is an illustration of a block diagram of the device 1 for wound assessment in accordance with an exemplary embodiment. As shown in FIG. 3, the device 1 can include a CPU (Central Processing Unit) 11, memory 12, for example, RAM (Random Access Memory), ROM (Read Only Memory), a 2D camera 12, a 3D camera, a display 15, a touch panel 16, a network interface 17, and a bus 18, which is configured to transfer data between components within the imaging device 1. In accordance with an exemplary embodiment, the imaging device 1 can include, for example, a power supply and other auxiliary electronics components. The network interface 17, for example, can include a wireless communication unit or networking unit, for example, can be a radio frequency (RF) and/or infrared (IR) transmission, and a networking interface, which can connect to a Local Area Network 19.

Figure 4:
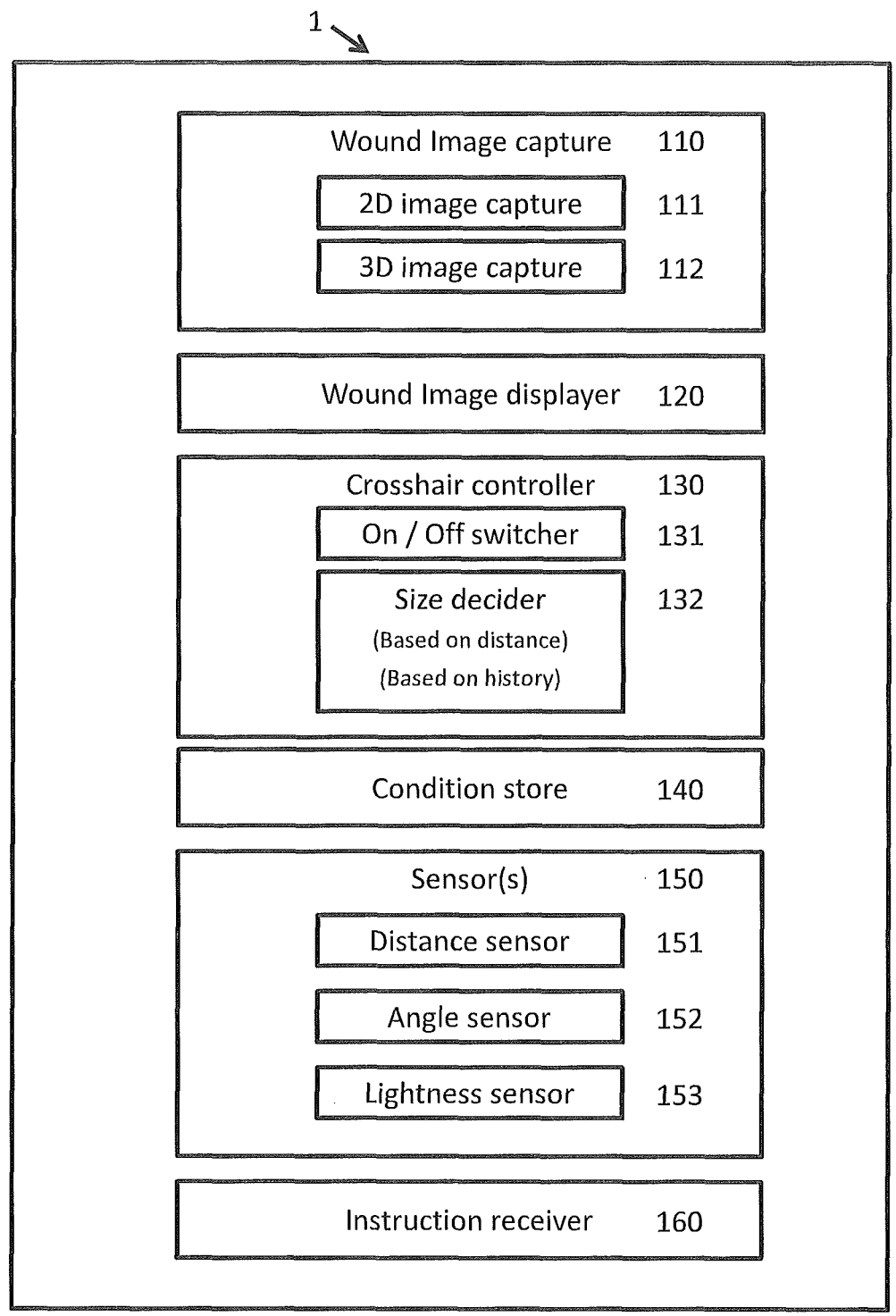
FIG. 4 is an illustration of a block diagram of a device for wound assessment showing functionality of device components in accordance with an exemplary embodiment.

FIG. 4 is an illustration of a block diagram of a device 1 for wound assessment showing functionality of the device components in accordance with an exemplary embodiment. As shown in FIG. 4, the device 1 can include a wound image capture module 110, a wound image displayer module 120, a crosshair controller module 130, a condition store module (e.g., memory) 140, sensor(s) 150, and an instruction receiver module 160.

In accordance with an exemplary embodiment, the wound image capture module 110 can include a 2D image capture module 111 and a 3D image capture module 112, which are configured to capture and process the images of the wound received from the 2D camera 13 and 3D camera 14. The crosshair controller module 130 can be configured to include an ON/OFF switcher, and wherein the crosshair is not displayed ("OFF"), if the present capturing environment does not correspond, for example to a stored condition. Alternatively, in an "ON" condition, the crosshair can be displayed if the present capturing environment corresponds to a stored condition. In addition, the crosshair controller module can include a size decider 132. For example, in accordance with an exemplary embodiment, the size decider 132 can be configured based on distance from the wound and/or history and/or stored condition of a wound, to adjust the size of the crosshair. The sensor(s) 150 can include, for example, a distance sensor 151, an angle sensor 152 for detecting movement of the imaging device 1, and a light or lightness sensor 153.

In accordance with an exemplary embodiment, for example, the instruction receiver 160 can be a touch screen panel or series of pixels with the word "SCAN", which sends a signal to the device to capture the image of the wound as disclosed herein.

Figures 5, 6:
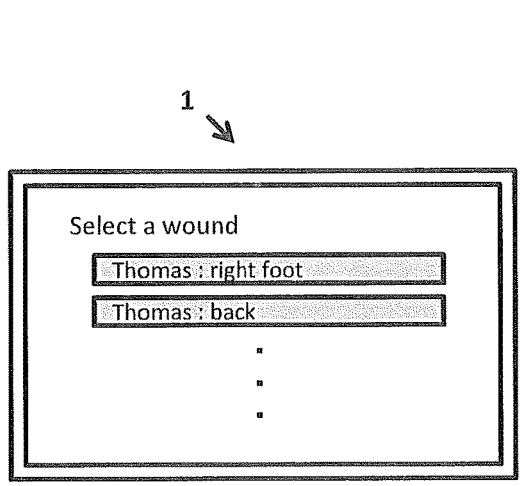
FIG. 5 is an illustration of an input screen in accordance with an exemplary embodiment.
FIG. 6 is an illustration of data, which can be stored in the device and output to a user via the user interface in accordance with an exemplary embodiment.

FIG. 5 is an illustration of an input screen in accordance with an exemplary embodiment. As shown in FIG. 5, the input screen can include, for example, a wound selection (i.e., "Select a wound"), and one or more wounds, for example, right and left foot, right and left leg, back, right and left arm, and/or right and left hand (i.e., "Thomas: right foot" and "Thomas: back").

FIG. 6 is an illustration of data, which can be stored in the device and output to a user via the user interface in accordance with an exemplary embodiment. As shown in FIG. 6, the condition data can include at least one of distance data, angle data, and lightness data. The condition data may be stored in connection with each user and/or wound location. In accordance with an exemplary embodiment, for example, it can be stored when the 3D image is constructed for the prior diagnosis, or can be stored, as a fix data for each imaging device 1 in advance.

FIG. 7 is an illustration showing wound detection history in accordance with an exemplary embodiment. As shown in FIG. 7, the result of the wound detection based on the 2D and 3D constructed data can be stored with respect to each diagnosis (or detection).

FIG. 8 is an illustration of a series of images depicted on the user interface in accordance with an exemplary embodiment. As shown in FIG. 8, upper figures, the crosshair is not displayed if the present capturing environment does not correspond to the stored condition. In the middle figures, the crosshair 40 is displayed if the present capturing environment corresponds to the stored condition. In addition, the distance between the 3D camera and the wound can be displayed. As shown in the bottom figures, in response to moving the device closer to the wound, the wound image is magnified. In addition, the size of the crosshair 40 is also magnified so that the size consists with a predetermined actual length. In accordance with an exemplary embodiment, the size of the crosshair 40 can be predetermined as fixed value, for example, 1 cm. In addition, in accordance with an exemplary embodiment, the size of the crosshair 40 can be determined by a wound detection history, for example, the prior detected wound size.

Figure 9:
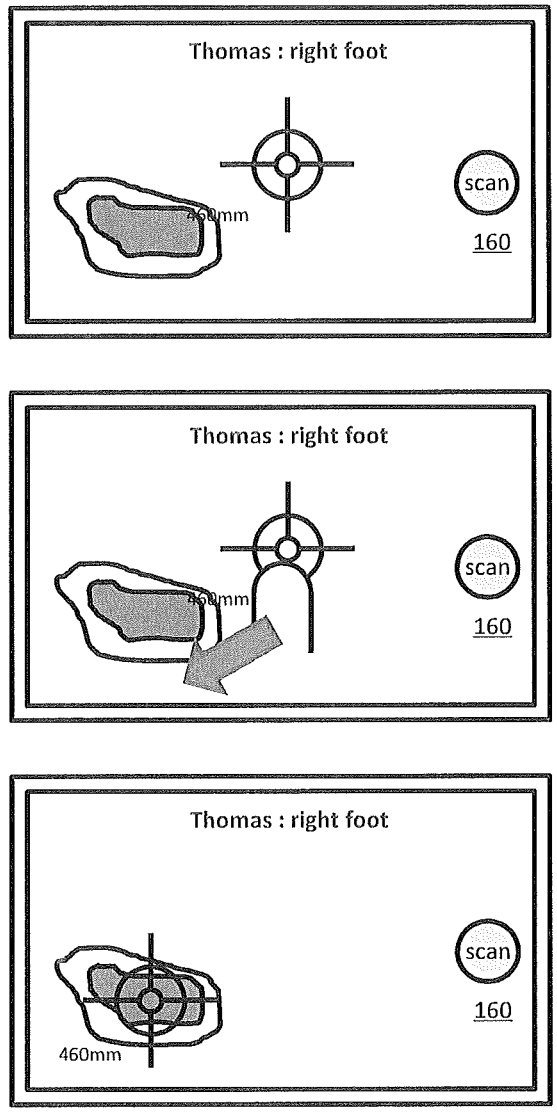
FIG. 9 is an illustration of a series of images depicted on the user interface in accordance with an exemplary embodiment.

FIG. 9 is an illustration of a series of images depicted on the user interface in accordance with an exemplary embodiment. In accordance with an exemplary embodiment, the crosshair can be manually moved with a fingertip of the operator on the touch screen to the wound. In response to the movement of the crosshair, the capturing range for which a 3D image is constructed moves so that a center of the capturing range corresponds to the crosshair.

Figure 10:
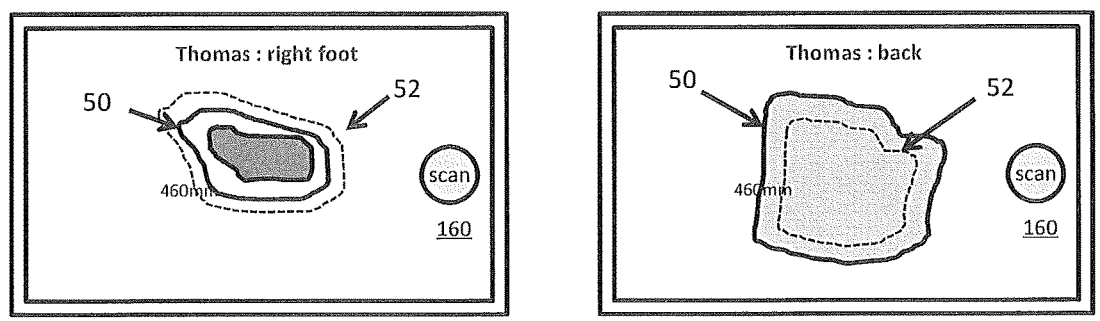
FIG. 10 is an illustration of a series of images depicted on the user interface in accordance with an exemplary embodiment.

FIG. 10 is an illustration of a series of images depicted on the user interface in accordance with an exemplary embodiment. As shown in FIG. 10, the shape 50 of the capturing region or bounding volume can be changed to a shape, which corresponds to the shape or region 52 previously detected in a prior diagnosis. In accordance with an exemplary embodiment, for example, a user can capture a wound image while comparing the wound to the shape 52 of the previously detected wound. In addition, together with the crosshair, the user can estimate wound size change at the same time.

Figure 11:
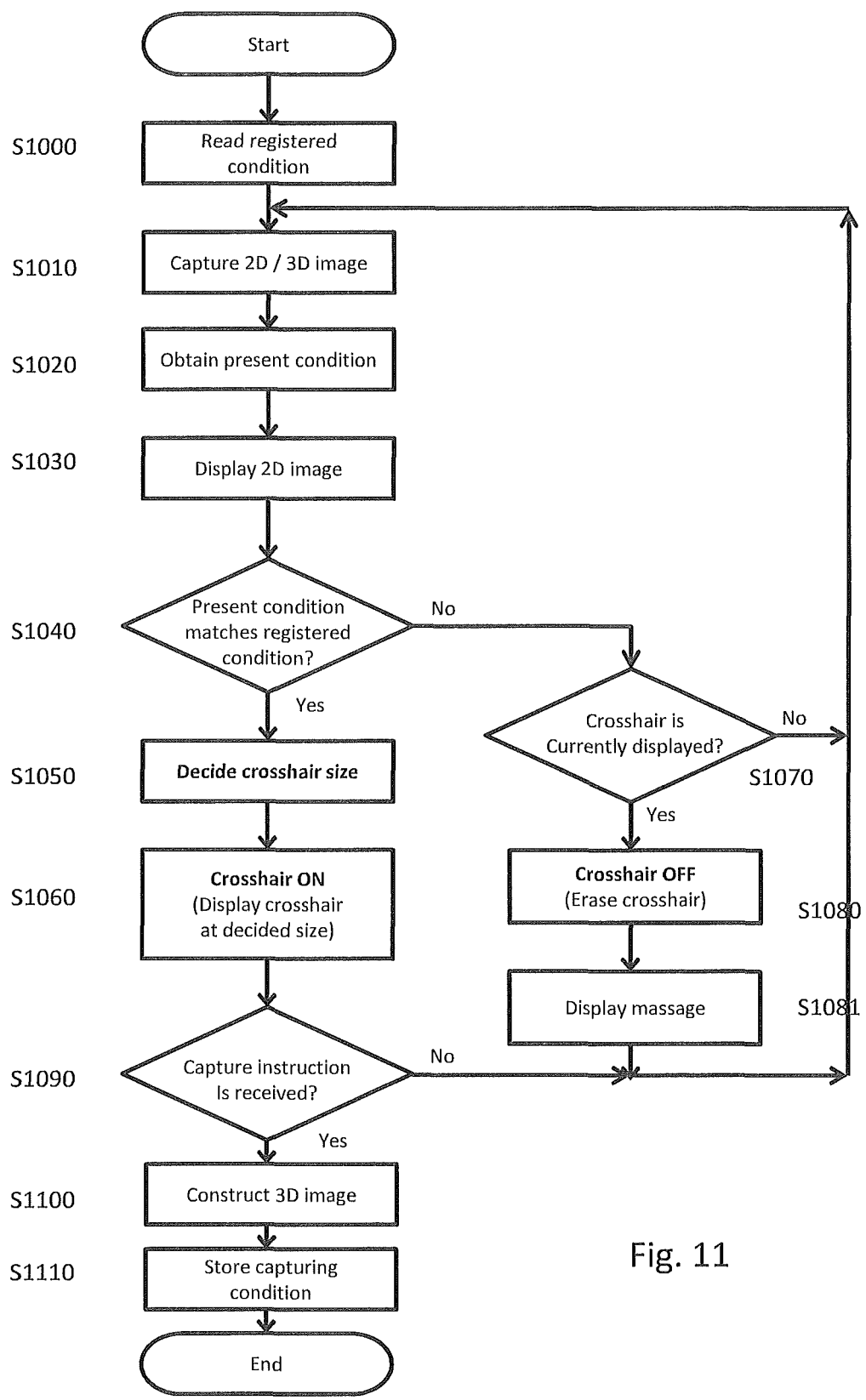
FIG. 11 is an illustration of a flow chart for wound assessment in accordance with an exemplary embodiment.

FIG. 11 is an illustration of a flow chart for wound assessment in accordance with an exemplary embodiment. As shown in FIG. 11, in step S1000, the registered condition is read, for example in response to a user selection on the user interface 15 (for example, FIG. 5) the registered condition corresponding to selected wound is read. In step S1100, 2D and 3D images are captured by the device 1. In step S1020, the present condition (present capturing environment) is obtained. In step S1030, a two-dimensional (2D) image is displayed on the user interface 15. In step S1040, a determination is made if the present condition matches the registered condition. If the present condition matches the registered condition, the process continues to step S1050, where the size of the crosshair is determined. In step S1060, with the crosshair "ON", i.e., crosshair is shown on the display screen, the crosshair is shown or displayed at the decided size. In step S1090, a determination is made if the captured instruction is received. If the captured instruction is received, the 3D image is constructed. In step S1110, the captured condition is stored.

If the present condition does not match the registered condition, the process continues to step S1070, where a determination is made if the crosshair is currently displayed. If yes, the cross is turned "OFF", the crosshair is erased, and in step S1081, a message (for example, Not match condition) can be displayed to the user.

In accordance with an exemplary embodiment, in step S1070, if the crosshair is not currently displayed, the process returns to step S1010 where the 2D and 3D images are captured.

In step S1090, if the captured image instructions is not received the process returns to step S1010, where 2D and 3D images are captured.

Figure 12:
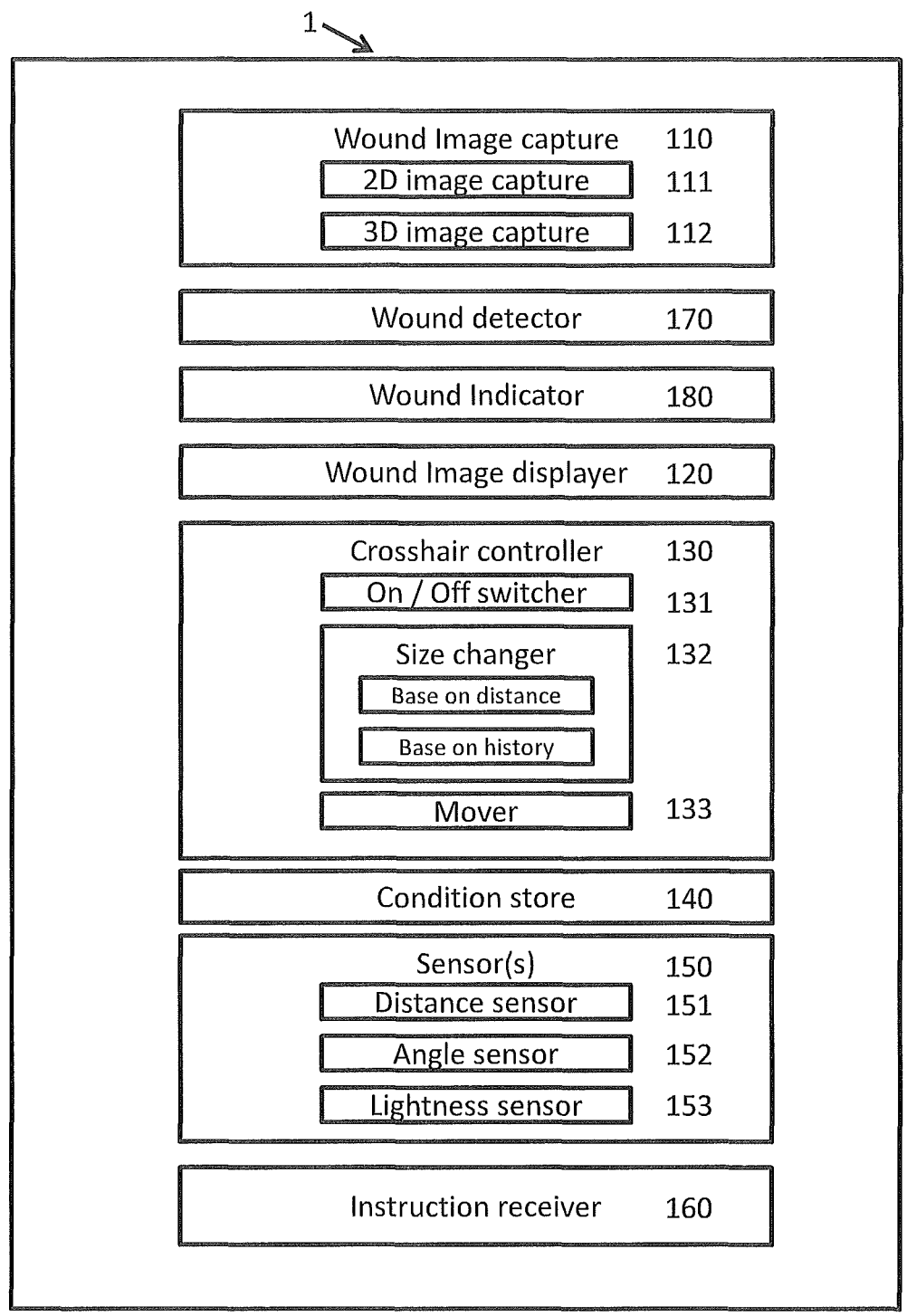
FIG. 12 is an illustration of a block diagram of a device for wound assessment showing functionality of device components in accordance with an exemplary embodiment.

FIG. 12 is an illustration of a block diagram of a device 1 for wound assessment showing functionality of device components in accordance with another exemplary embodiment. As shown in FIG. 12, the device 1 can include a wound image capture module 110, a wound image displayer module 120, a crosshair controller module 130, a condition store module (e.g., memory) 140, sensor(s) 150, an instruction receiver module 160, a wound detector module 170, and a wound indicator module 180.

In accordance with an exemplary embodiment, the wound image capture module 110 can include a 2D image capture module 111 and a 3D image capture module 112, which are configured to capture and process the images of the wound received from the 2D camera 13 and 3D camera 14. The crosshair controller module 130 can be configured to include an ON/OFF switcher, and wherein the crosshair is not displayed ("OFF"), if the present capturing environment does not correspond, for example to a stored condition. Alternatively, in an "ON" condition, the crosshair can be displayed if the present capturing environment corresponds to a stored condition or a new wound. In addition, the crosshair controller module can include a size decider 132. For example, in accordance with an exemplary embodiment, the size decider 132 can be configured based on distance from the wound and/or history and/or stored condition of a wound, to adjust the size of the crosshair. In addition, a mover module 133 can be included within the crosshair controller module 130, which allows the user to manually move the crosshair. The sensor(s) 150 can include, for example, a distance sensor 151, an angle sensor 152 for the device 1, and a lightness sensor 153.

Figure 13:
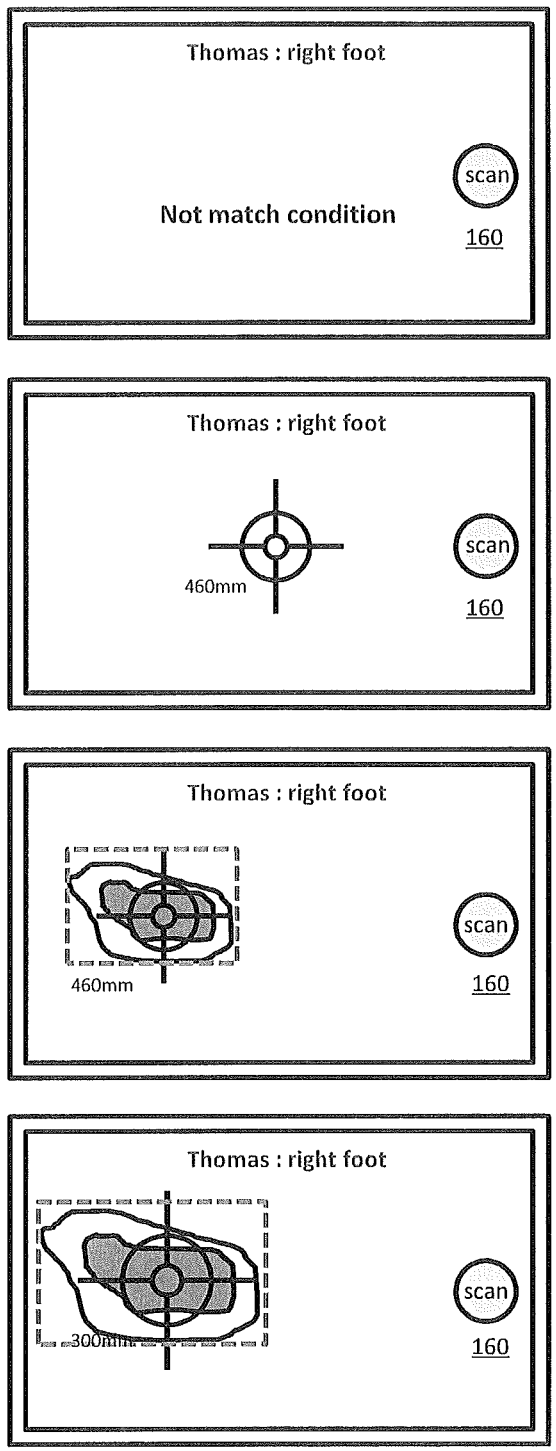
FIG. 13 is an illustration of a series of images depicted on the user interface in accordance with an exemplary embodiment.

FIG. 13 is an illustration of a series of images depicted on the user interface illustrating the use of the wound detector module 170 and the wound indicator 180. As shown in the upper figure of FIG. 13, if no match is detected, the crosshair is not shown. Alternatively, the crosshair is displayed if the present capturing environment corresponds to the stored condition. In addition, the distance between the 3D camera and the wound is displayed on the display panel 15. In accordance with an exemplary embodiment, when a wound is detected, the wound indicator is displayed at the position of the detected wound, and the crosshair is moved to the center of the wound.

As shown in the above example, the crosshair is displayed in response to the present environment corresponding to the stored condition; however, other embodiments may be employed. For example, the crosshair may not be displayed while no wound is detected even if the present environment corresponds to the stored condition, and then, both of the crosshair and the wound indicator may be concurrently displayed when the present environment corresponds to the stored condition and a wound is detected. In accordance with another exemplary embodiment, the wound indicator may be displayed when a wound is detected even though the present environment does not correspond to the stored condition, and then the crosshair may be overlapped in response to that the present environment corresponds to the stored condition.

Figure 14:
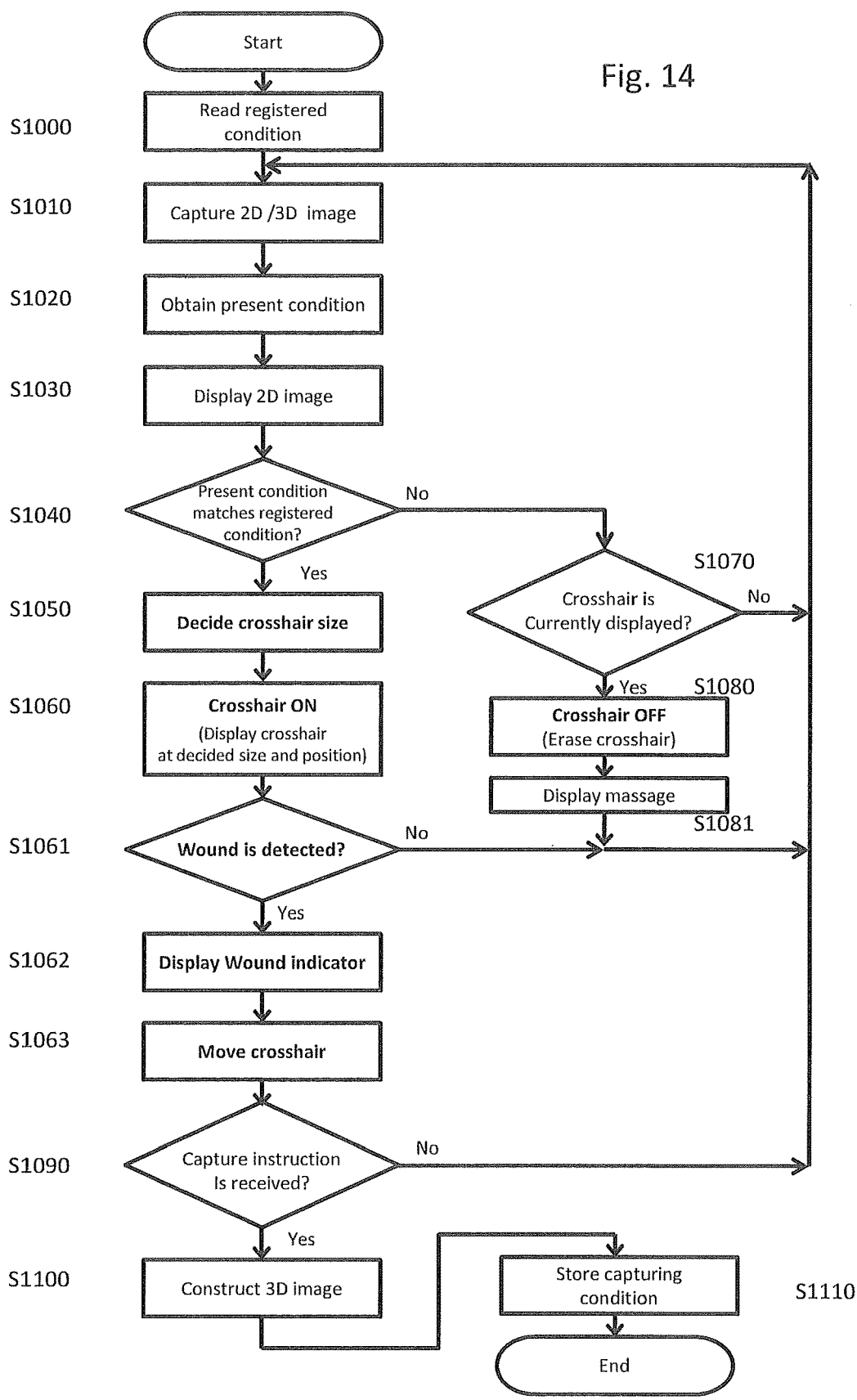
FIG. 14 is an illustration of a flow chart for wound assessment in accordance with an exemplary embodiment.

FIG. 14 is an illustration of a flow chart for wound assessment in accordance with an exemplary embodiment. As shown in FIG. 14, the process is similar to the process as shown in FIG. 11, however, in step S1060, the wound detector module 170, when the crosshair is "ON" and displayed at a decided or determined size and position, in step 1061, a determination can be made if the wound is detected. If the wound is not detected, the process continues to step S1010, where the 2D and 3D images are captured. However, if the wound is detected, in step S1062, the wound indication is displayed and in step S1063, the crosshair can be moved to the wound on the display panel 15. The process continues to step S1090, where a determination is made, if the capture instruction, i.e., the SCAN icon or series are activated, for example, on the touch panel 16.

Figure 15:
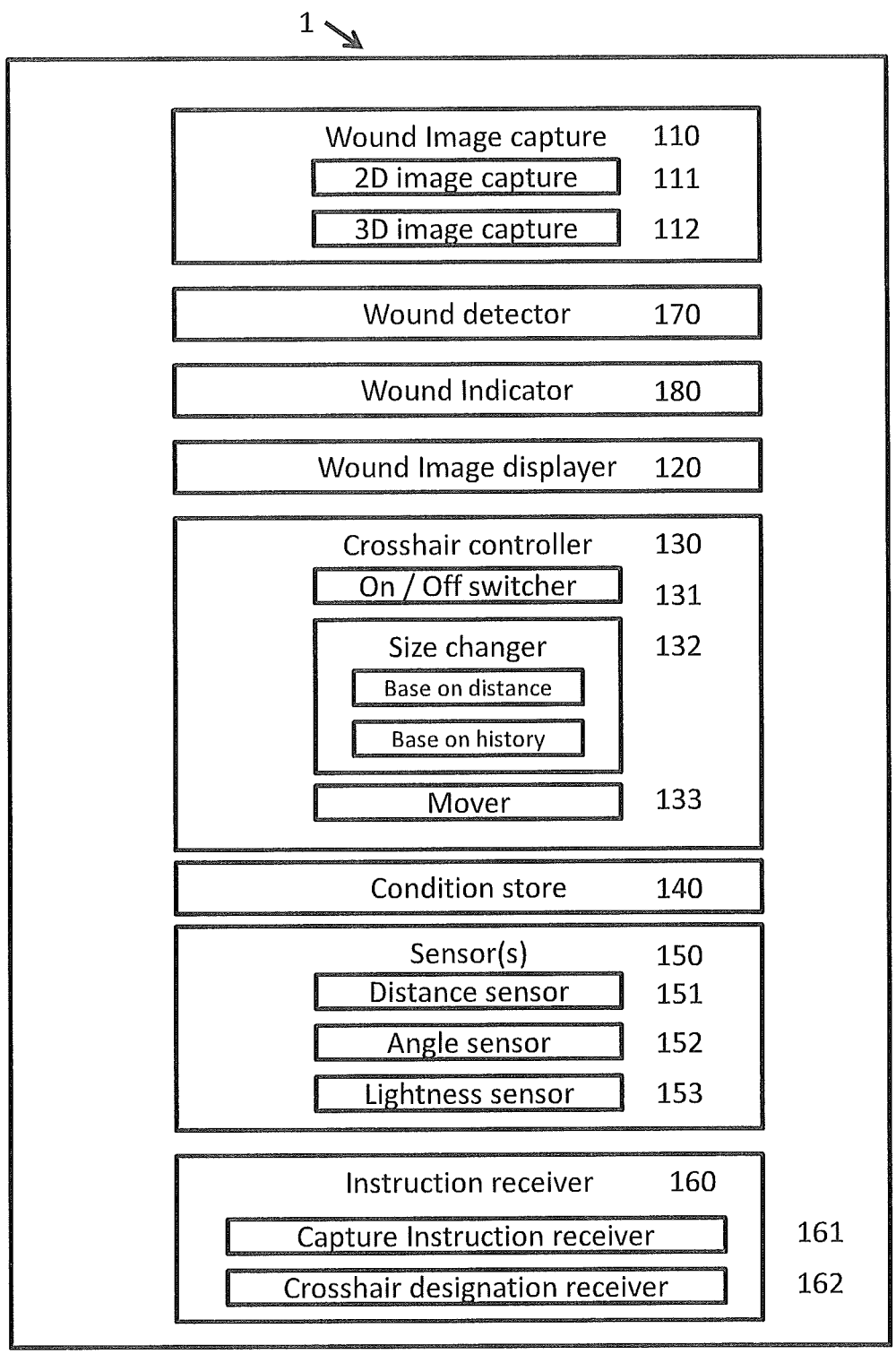
FIG. 15 is an illustration of a block diagram of a device for wound assessment showing functionality of device components in accordance with an exemplary embodiment.

FIG. 15 is an illustration of a block diagram of a device for wound assessment showing functionality of device components in accordance with an exemplary embodiment. As shown in FIG. 15, the device 1 can include the modules as shown in FIGS. 4 and 12, however, the instruction receiver module 160 can include a capture instruction receiver (or SCAN icon) 161, and a crosshair designation receiver 162. The crosshair designation receiver 162 can be configured such that crosshair can be manually moved on the display panel 15, if, for example, two or more wounds are present in the image.

Figure 16:
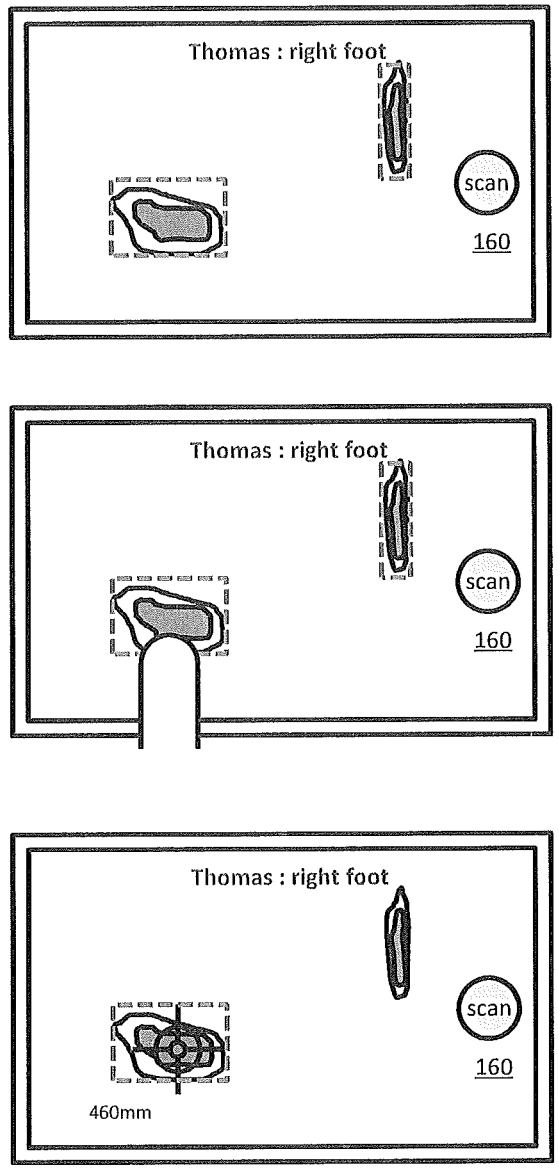
FIG. 16 is an illustration of a series of images depicted on the user interface in accordance with an exemplary embodiment.

FIG. 16 is an illustration of a series of images depicted on the user interface in accordance with an exemplary embodiment. As shown, in accordance with an exemplary embodiment, two or more wounds can be present in a single image. In accordance with an exemplary embodiment, the crosshair designation receiver 162 can be configured, such that via the touch screen 16, one of the two or more wounds on the display panel 15 can be selected. For example, by activation of the crosshair designation receiver 162, by touching one of the two images, the crosshair will move and/or relocate to the selected image.

Figure 17A:
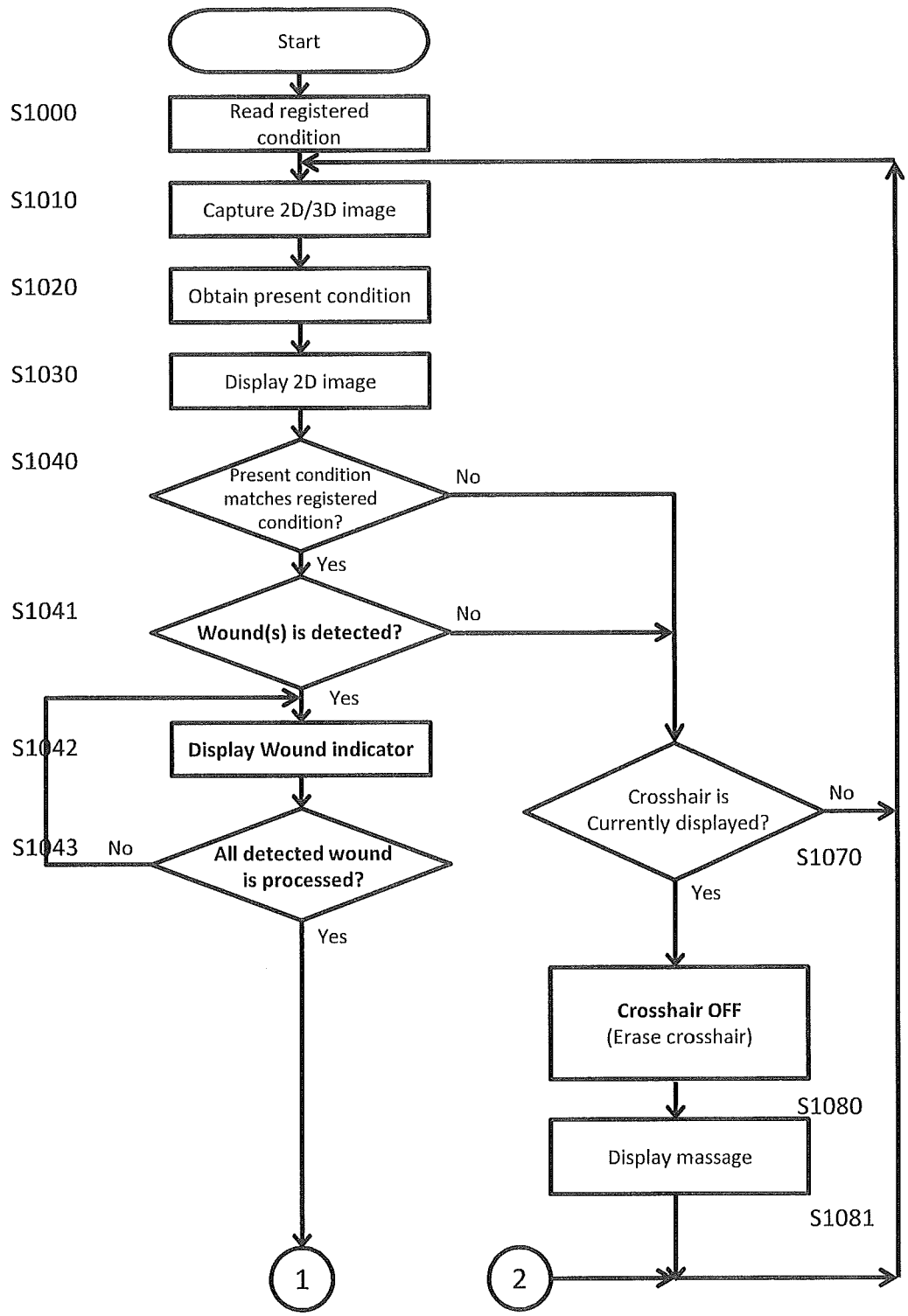
FIGS. 17A and 17B are illustrations of a flow chart for wound assessment in accordance with an exemplary embodiment.
Figure 17B:
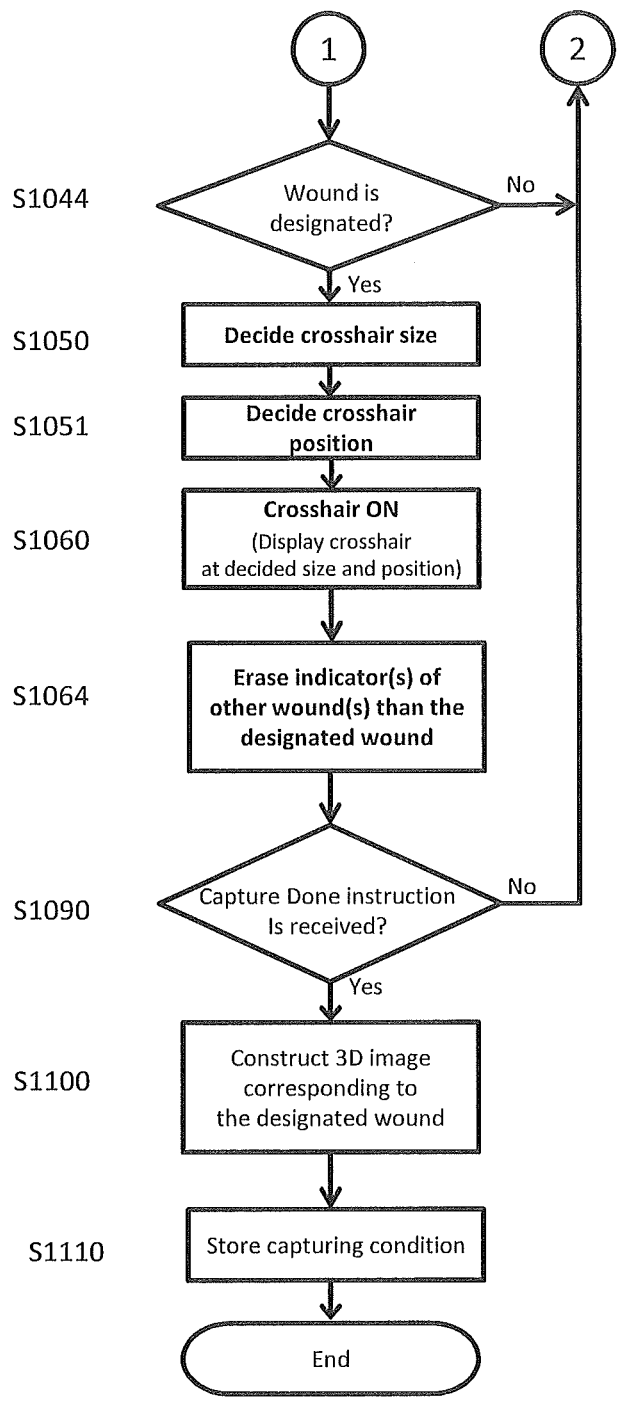

FIGS. 17A and 17B are illustrations of a flow chart for wound assessment in accordance with an exemplary embodiment. As shown in FIGS. 17A and 17B, the process is similar to the process as shown in FIGS. 11 and 14, however, in step S1041, the wound detector module 170, determines if one or more wounds are present. If no wounds are detected, the process continues to step S1070, where a determination is made, if the crosshair is currently displayed as described in accordance with FIG. 11. Alternatively, if one or more wounds are detected in step S1041, the process continues to step S1042, wherein the wound indicator is displayed. In step S1043, if all the detected wounds are processed, the process continues to step S1044, where a determination is made if the wound has be designated and/or selected. If the wound has not been designated or selected, the process continues to step S1010, where the 2D and 3D images are captured.

In accordance with an exemplary embodiment, if the wound has been designated or selected, in step S1050, the crosshair size is decided or determined, and the in step S1051, the crosshair position can be decided or determined. The process continues to step S1060, where the crosshair is activated or "ON" and in step S1064, the crosshair designation receiver 162 in combination with the wound detector module 170 and the wound indicator module 180, can erase and/or deleted wounds on the display panel, which are not designated and/or selected. The process continues to step S1090, wherein it is determined if the capture instructions is received as described in connection with FIG. 11.

In accordance with an exemplary embodiment, a computer program product comprising a non-transitory computer usable medium having a computer readable code embodied therein is disclosed for capturing an image of a wound on a subject for wound assessment, the process comprising: obtaining an image of a portion of the subject with one or more cameras; displaying the image on a display panel on an imaging device; obtaining a stored condition from a memory, the stored condition including at least one of distance data, angle data, and lightness data; obtaining a present condition; comparing the stored condition and the present condition; displaying a crosshair over the image on the display panel when it is decided that the present condition corresponds to the stored condition on the basis of the comparison; receiving an instruction for capturing; and capturing an image of the wound in response to the received instruction.

The non-transitory computer usable medium, of course, may be a magnetic recording medium, a magneto-optic recording medium, or any other recording medium which will be developed in future, all of which can be considered applicable to the present invention in all the same way. Duplicates of such medium including primary and secondary duplicate products and others are considered equivalent to the above medium without doubt. Furthermore, even if an embodiment of the present invention is a combination of software and hardware, it does not deviate from the concept of the invention at all. The present invention may be implemented such that its software part has been written onto a recording medium in advance and will be read as required in operation.

It will be apparent to those skilled in the art that various modifications and variation can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of capturing an image of a wound on a subject for wound assessment, the method comprising:
   obtaining an image of a portion of the subject with one or more cameras;
   displaying the image on a display panel on an imaging device, the display panel including a touch screen;
   obtaining a stored condition from a memory, the memory being within the imaging device, or the memory being an external memory, which is in communication with the imaging device via a network interface on the imaging device;
   obtaining a present condition;
   comparing the stored condition and the present condition;
   displaying a crosshair over the image on the display panel when the present condition corresponds to the stored condition on a basis of the comparison and removing the crosshair from the display panel when the present condition does not correspond to the stored condition on the basis of the comparison;
   displaying a distance from the wound to the imaging device on the display panel;
   receiving an instruction for capturing when the present condition corresponds to the stored condition; and
   capturing the image of the wound in response to the received instruction.

2. The method according to claim 1, wherein the stored condition includes at least one of distance data, angle data, and lightness data.

3. The method according to claim 2, comprising:
   storing the stored condition when the image of the wound is captured, and
   reading the stored condition for a next capturing.

4. The method according to claim 2, comprising:
   displaying a condition selection menu on the display panel, the condition selection menu providing a list of one or more previously captured wounds for the subject; and
   obtaining the stored condition corresponding to a selection on the condition selection menu.

5. The method according to claim 1, comprising:
   changing a size of the crosshair on a basis of the distance from the wound to the imaging device so that the size of the crosshair consists with a predetermined actual length.

6. The method according to claim 5, comprising:
   setting the predetermined actual length of the crosshair based on a wound detection history of one or more previously captured wounds.

7. The method according to claim 5, comprising:
   setting the predetermined actual length of the crosshair to a fixed value.

8. The method according to claim 1, comprising:
   providing a capture range and a capture shape on the display panel to assist with the capturing of the image of the wound.

9. The method according to claim 8, wherein the capture shape has a shape of a cuboid, sphere, or ellipsoid; and
   matching the capture shape to the wound.

10. The method according to claim 1, comprising:
    locating the crosshair at a center of the wound on the display panel; and
    capturing the image of the wound while the crosshair is located on the center of the wound on the display panel.

11. The method according to claim 1, comprising:
    manually moving the crosshair to the wound on the display panel using the touch screen; and
    dragging the crosshair to the image of the wound or tapping on the image of the wound to move the crosshair to the wound.

12. The method according to claim 1, comprising:
    varying a shape of a bounding volume based on a shape corresponding to a shape of the wound from a prior imaging.

13. The method according to claim 1, comprising:
    highlighting the wound with a color to assist the user in capturing the wound.

14. The method according to claim 1, wherein the crosshair is a represented by intersecting lines in the shape of a cross, a "+", dots, posts, circles, scales, chevrons, a combination of the cross, the "+", the dots, the posts, the circles, the scales, and the chevrons.

15. A computer program product comprising a non-transitory computer usable medium having a computer readable code embodied therein for capturing an image of a wound on a subject for wound assessment, the process comprising:
    obtaining an image of a portion of the subject with one or more cameras;

displaying the image on a display panel on an imaging device, the display panel including a touch screen;

obtaining a stored condition from a memory, the stored condition including at least one of distance data, angle data, and lightness data, the memory being within the imaging device, or the memory being an external memory, which is in communication with the imaging device via a network interface on the imaging device;

obtaining a present condition;

comparing the stored condition and the present condition;

displaying a crosshair over the image on the display panel when the present condition corresponds to the stored condition on a basis of the comparison and removing the crosshair from the display panel when the present condition does not correspond to the stored condition on the basis of the comparison;

displaying a distance from the wound to the imaging device on the display panel;

receiving an instruction for capturing when the present condition corresponds to the stored condition; and capturing the image of the wound in response to the received instruction.

16. An imaging device for capturing an image of a wound on a subject for wound assessment, the imaging device comprising:
- one or more cameras configured to obtain an image of a portion of the subject with one or more cameras;
- displaying the image on a display panel on the imaging device, the display panel including a touch screen; and
- a processor configured to:
  - obtain a stored condition from a memory, the memory being within the imaging device, or the memory being an external memory, which is in communication with the processor via a network interface on the imaging device;
  - obtain a present condition;
  - compare the stored condition and the present condition;
  - display a crosshair over the image on the display panel when the present condition corresponds to the stored condition on a basis of the comparison and removing the crosshair from the display panel when the present condition does not correspond to the stored condition on the basis of the comparison;
  - display a distance from the wound to the imaging device on the display panel;
  - receive an instruction for capturing when the present condition corresponds to the stored condition; and
  - capture the image of the wound in response to the received instruction.

17. The imaging device according to claim 16, wherein the stored condition includes at least one of distance data, angle data, and lightness data.

18. The imaging device according to claim 17, wherein the processor is configured to:
- store the stored condition when the image of the wound is captured;
- read the stored condition for a next capturing;
- displaying a condition selection menu on the display panel, the condition selection menu providing a list of one or more previously captured wounds for the subject; and
- obtaining the stored condition corresponding to a selection on the condition selection menu.

* * * * *